(12) United States Patent
Beeckler et al.

(10) Patent No.: US 11,160,607 B2
(45) Date of Patent: Nov. 2, 2021

(54) HYPER-APERTURED ABLATION ELECTRODE

(71) Applicant: BIOSENSE WEBSTER (ISRAEL) LTD., Yokneam (IL)

(72) Inventors: Christopher Thomas Beeckler, Brea, CA (US); Joseph Thomas Keyes, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 838 days.

(21) Appl. No.: 14/947,378

(22) Filed: Nov. 20, 2015

(65) Prior Publication Data

US 2017/0143411 A1   May 25, 2017

(51) Int. Cl.
   *A61B 18/14*   (2006.01)
   *B23K 26/382*   (2014.01)
   (Continued)

(52) U.S. Cl.
   CPC ........ *A61B 18/1492* (2013.01); *A61B 8/0858* (2013.01); *A61B 8/0883* (2013.01);
   (Continued)

(58) Field of Classification Search
   CPC ... B23K 26/382; A61B 18/14; A61B 18/1442; A61B 18/1445; A61B 18/1448; A61B 18/1492; A61B 2018/00029; A61B 2018/00065; A61B 2018/00351; A61B 2018/00577; A61B 2018/00642; A61B 2018/00904; A61B 2018/00994; A61B 2017/00044; A61B 2017/00526; A61B 2218/002; A61B 8/0858; A61B 8/0883; A61B 8/12; A61B 8/445; A61B 8/4483
   (Continued)

(56) References Cited

U.S. PATENT DOCUMENTS

| 5,630,268 A | 5/1997 | Smith et al. |
| 7,824,402 B2 | 11/2010 | Vaska et al. |

(Continued)

FOREIGN PATENT DOCUMENTS

| CN | 101495056 A | 7/2009 |
| CN | 101862236 A | 10/2010 |

(Continued)

OTHER PUBLICATIONS

NDT Supply, Chapter 5 "Ultrasonic Inspection Method", pp. 5-1-5-103.*

(Continued)

*Primary Examiner* — Michael F Peffley
*Assistant Examiner* — Khadijeh A Vahdat
(74) *Attorney, Agent, or Firm* — Notaro, Michalos & Zaccaria P.C.

(57) ABSTRACT

Ablation apparatus is provided. The apparatus includes an ablation electrode shaped to define a cavity thereof, and comprising a metallic distal face that is shaped to define a plurality of apertures. A fluid-delivery channel is configured to deliver fluid to the apertures. At least one ultrasound transducer is disposed within the cavity of the ablation electrode, the transducer being configured to transmit an ultrasound wave through the apertures. Other embodiments are also described.

8 Claims, 5 Drawing Sheets

(51) Int. Cl.
*A61B 8/08* (2006.01)
*A61B 8/12* (2006.01)
*A61B 8/00* (2006.01)
*A61B 17/00* (2006.01)
*A61B 18/00* (2006.01)

(52) U.S. Cl.
CPC ............... *A61B 8/12* (2013.01); *A61B 8/445* (2013.01); *A61B 8/4483* (2013.01); *B23K 26/382* (2015.10); *A61B 2017/00044* (2013.01); *A61B 2017/00526* (2013.01); *A61B 2018/00029* (2013.01); *A61B 2018/00065* (2013.01); *A61B 2018/00351* (2013.01); *A61B 2018/00577* (2013.01); *A61B 2018/00642* (2013.01); *A61B 2018/00904* (2013.01); *A61B 2018/00994* (2013.01); *A61B 2218/002* (2013.01)

(58) Field of Classification Search
USPC ....................................................... 606/33–50
See application file for complete search history.

(56) References Cited

U.S. PATENT DOCUMENTS

| | | | | |
|---|---|---|---|---|
| 7,918,850 | B2* | 4/2011 | Govari | A61B 18/1492 606/34 |
| 2002/0049438 | A1 | 4/2002 | Sharkey et al. | |
| 2002/0151885 | A1 | 10/2002 | Underwood | |
| 2003/0144656 | A1* | 7/2003 | Ocel | A61B 5/042 606/41 |
| 2003/0225443 | A1 | 12/2003 | Kiran et al. | |
| 2005/0256518 | A1* | 11/2005 | Rama | A61B 17/2202 606/27 |
| 2010/0030209 | A1* | 2/2010 | Govari | A61B 18/1492 606/34 |
| 2011/0264089 | A1* | 10/2011 | Zirkle | A61B 5/6852 606/41 |
| 2012/0004547 | A1* | 1/2012 | Harks | A61B 8/0858 600/439 |
| 2012/0265192 | A1* | 10/2012 | Sliwa | A61B 8/12 606/33 |
| 2013/0310823 | A1 | 11/2013 | Gelfand et al. | |
| 2014/0058386 | A1* | 2/2014 | Clark | A61B 18/14 606/41 |

FOREIGN PATENT DOCUMENTS

| | | |
|---|---|---|
| CN | 102481170 A | 5/2012 |
| CN | 102781358 A | 11/2012 |
| CN | 202751442 U | 2/2013 |
| CN | 104768489 A | 7/2015 |
| EP | 1 820 464 A1 | 8/2007 |
| EP | 2 145 596 A1 | 1/2010 |
| JP | 2007537832 A | 12/2007 |
| JP | 2010022825 A | 2/2010 |
| JP | 2011125707 A | 6/2011 |
| JP | 2013502967 A | 1/2013 |
| WO | WO 2011/024133 A1 | 3/2011 |
| WO | WO 2013/102072 A1 | 7/2013 |
| WO | WO 2014/072879 A2 | 5/2014 |

OTHER PUBLICATIONS

European Search Report dated Apr. 11, 2017 from corresponding European Patent Application No. 16199498.3.

Wright, Matt et al., "Intra-tissue Ablation & Visualization System to Monitor Lesion Formation", Presentation at Heart Rhythm Society Meeting—Heart Rhythm on Demand 2013, May 10, 2013.

Chinese search report and office action for corresponding Chinese patent application No. 201611031290.1, dated Jun. 29, 2020.

Chinese office action for corresponding Chinese patent application No. 201611031290.1, dated Feb. 3, 2021.

Japanese office action for corresponding Japanese patent application No. 2016-224958, dated Nov. 24, 2020.

* cited by examiner

HYPER-APERTURED ABLATION ELECTRODE

FIELD OF THE INVENTION

The present invention relates to medical procedures, particularly ablation procedures.

BACKGROUND

Minimally-invasive intracardiac ablation is the treatment of choice for various types of arrhythmias. During such treatments, lesions, which are not electrically conductive, are formed in cardiac tissue. The lesions disrupt abnormal electrical pathways in the tissue, thus disrupting the abnormal electrical signals that trigger the arrhythmia. Ablation may be used to treat, for example, supraventricular tachycardia, Wolff-Parkinson-White syndrome, ventricular tachycardia, and atrial fibrillation.

US 2013/0310823 to Gelfand, whose disclosure is incorporated herein by reference, describes systems, devices, and methods for treating a patient having a sympathetically mediated disease associated at least in part with augmented peripheral chemoreflex or heightened sympathetic activation. The treatments include ablating one or more peripheral chemoreceptors or associated afferent nerves to reduce or remove afferent neural signals from the peripheral chemoreceptor.

U.S. Pat. No. 7,824,402 to Vaska, whose disclosure is incorporated herein by reference, describes an ablating device having a cover which holds an interface material such as a gel. The cover contains the interface material during initial placement of the device. The ablating device may also have a removable tip or a membrane filled with fluid. In still another aspect, the ablating device may be submerged in liquid during operation.

US 2003/0225443 to Kiran, whose disclosure is incorporated herein by reference, describes methods and devices for modulating atrial configuration, e.g., changing the configuration of an atrium, for example by reducing the volume of a left or right atrium. In practicing the subject methods, the configuration of an atrium is modified or changed at least partially without the use of an implant, e.g., through chemical modification and/or application of energy to atrial tissue, where representative energy sources include RF, microwave, laser, ultrasound, cryoablative energy sources, etc. In certain embodiments, the desired atrial configuration modification is achieved by reduction of the atrial volume, e.g., through reduction of the volume of, or constricting/closing the entrance to, the atrial appendage thereof, in a manner sufficient to reduce the volume of the atrium. In certain embodiments, a catheter device comprising an RF source is employed to modulate atrial configuration according to the subject methods. Also provided are devices, systems and kits for use in practicing the subject methods. The subject methods, devices, systems and kits find use in a variety of applications, including reducing the risk of stroke in a subject suffering from atrial fibrillation.

SUMMARY OF THE INVENTION

There is provided, in accordance with some embodiments of the present invention, ablation apparatus. The apparatus includes an ablation electrode shaped to define a cavity thereof, and including a metallic distal face that is shaped to define a plurality of apertures. The apparatus further includes a fluid-delivery channel, configured to deliver fluid to the apertures, and at least one ultrasound transducer disposed within the cavity of the ablation electrode, the transducer being configured to transmit an ultrasound wave through the apertures.

In some embodiments, a total surface area of the apertures is at least 20% of a total surface area of the distal face.

In some embodiments, the total surface area of the apertures is less than 50% of the total surface area of the distal face.

In some embodiments, the distal face is shaped to define at least 100 apertures.

In some embodiments, the distal face is shaped to define at least 200 apertures.

In some embodiments, a surface area of each of the apertures is less than 0.2% of a total surface area of the distal face.

In some embodiments, a thickness of the distal face is between 0.075 and 0.5 mm.

In some embodiments, the distal face includes a mesh.

In some embodiments, part of the mesh defines a side wall of the ablation electrode.

In some embodiments, the transducer is disposed at least 0.5 mm from the distal face.

In some embodiments, the at least one ultrasound transducer includes a plurality of ultrasound transducers.

In some embodiments, the plurality of ultrasound transducers includes an array of ultrasound transducers.

There is further provided, in accordance with some embodiments of the present invention, a method for ablating tissue of a patient. An ablation electrode is inserted into the patient, the electrode including a distal face that is shaped to define a plurality of apertures. Subsequently, at least one ultrasound wave is transmitted, from at least one ultrasound transducer disposed within a cavity of the ablation electrode, through the apertures. In response to reflections of the ultrasound wave received by the transducer, a thickness of tissue of the patient is estimated. In response to the estimated thickness, a property of an ablating current is set. The ablating current is passed from at least the distal face of the ablation electrode into the tissue, while a fluid is passed out of the ablation electrode, through the apertures.

In some embodiments, the fluid includes a saline fluid.

In some embodiments, transmitting the at least one ultrasound wave includes transmitting the at least one ultrasound wave while passing the ablating current.

In some embodiments, passing the ablating current from at least the distal face includes passing the ablating current from between the apertures.

In some embodiments, the tissue includes cardiac tissue.

In some embodiments, the method further includes using the distal face to sense electrical activity of the tissue.

In some embodiments, the at least one ultrasound transducer includes an array of ultrasound transducers, and transmitting the at least one ultrasound wave includes transmitting the at least one ultrasound wave by transmitting an ultrasound beam from the array of ultrasound transducers.

In some embodiments, transmitting the ultrasound beam from the array of ultrasound transducers includes transmitting the ultrasound beam at a non-zero angle with respect to a central longitudinal axis of the ablation electrode.

There is further provided, in accordance with some embodiments of the present invention, a method for forming an ablation electrode. An element shaped to define a cavity thereof is provided. A face that is shaped to define a plurality of apertures is formed at a distal end of the element. At least one ultrasound transducer is placed into the cavity of the element, and a fluid-delivery channel, configured to deliver fluid to the apertures, is coupled to the element.

In some embodiments, forming the face includes forming the face by making at least 100 perforations in the distal end of the element.

In some embodiments, forming the face includes forming the face by making at least 200 perforations in the distal end of the element.

In some embodiments, making the perforations includes making the perforations by laser-drilling the perforations.

In some embodiments, making the perforations includes making the perforations by use of electrical discharge machining.

In some embodiments, forming the face includes forming the face by attaching a mesh at the distal end of the element.

The present invention will be more fully understood from the following detailed description of embodiments thereof, taken together with the drawings, in which:

DETAILED DESCRIPTION OF EMBODIMENTS

Overview

Figure 1:
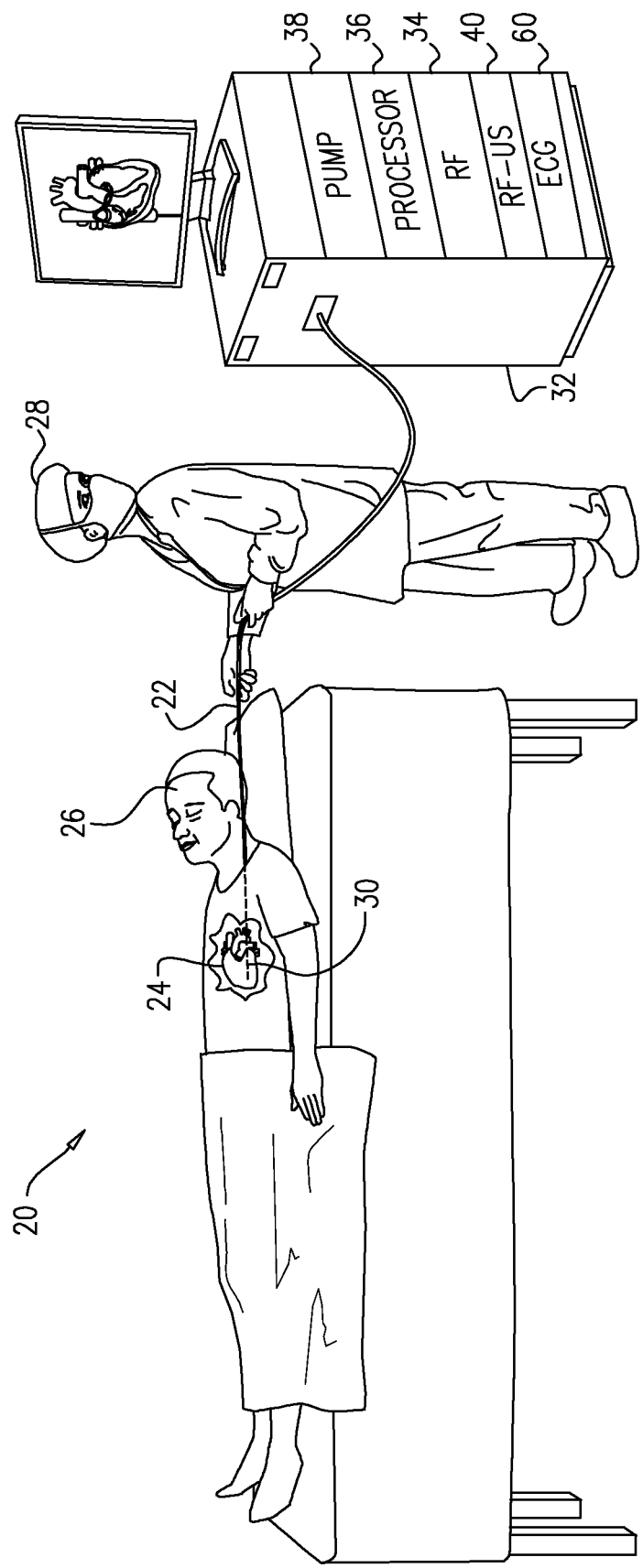
FIG. 1 is a schematic pictorial illustration of a system for cardiac ablation treatment, in accordance with some embodiments of the present invention.

In embodiments of the present invention, an intra-body probe (e.g., a catheter) is inserted into a patient, the intra-body probe comprising an ablation electrode at a distal end thereof. The ablation electrode is brought into contact with tissue of the patient, and subsequently, an ablating current is passed from the ablation electrode (e.g., at least from the distal face of the electrode, such as from the entire surface of the electrode), into the tissue, thus resistively heating the tissue to create an electrically non-conductive lesion in the tissue. While the ablating current is passed into the tissue, an irrigating fluid may be passed out of the ablation electrode and into the blood in the vicinity of the electrode, thus cooling and diluting the blood to help prevent the blood from clotting.

It is often helpful to estimate the thickness of the tissue prior to, and/or while, passing the ablating current into the tissue, in that a property of the ablating current, such as the power and/or duration of the ablating current, may be set in response to the estimated thickness, in order to achieve a transmural lesion while reducing the risk of damaging externally adjacent structures. Hence, in embodiments of the present invention, an ultrasound transducer is disposed within a cavity of the ablation electrode. The transducer transmits an ultrasound wave that is reflected from the tissue, and based on reflections of the wave that are detected by the transducer, the thickness of the tissue is estimated.

One option for positioning the ultrasound transducer is to place the ultrasound transducer at an opening in the distal face of the ablation electrode. However, the presence of such an opening, which would need to be relatively large in order to accommodate the transducer, would leave relatively little surface area of the distal face remaining for application of the ablating current. Furthermore, the transducer might block the opening, thus preventing irrigating fluid from being passed out of the opening. Even if the transducer were moved back from the opening to allow for passage of the irrigating fluid, the flow of irrigating fluid from such a large opening would be difficult to control.

A more advantageous option, provided by embodiments of the present invention, is to make the distal face of the ablation electrode "hyper-apertured," such that the distal face is shaped to define a relatively large number of apertures. At least one ultrasound transducer may then be disposed within the cavity of the ablation electrode, slightly recessed from the hyper-apertured distal face. Thus, embodiments of the present invention provide at least the following advantages:

(i) The apertures in the distal face allow the ultrasound wave from the transducer, as well as the reflections from the tissue, to pass through the distal face without being overly attenuated.

(ii) While the ablating current is passed into the tissue, irrigating fluid may be passed out of the apertures.

(iii) The ablating current may be passed from the hyper-apertured distal face, and/or the hyper-apertured distal face may be used to sense electrical activity of the tissue.

(iv) The hyper-apertured distal face may shield the transducer from mechanical forces that might otherwise damage the transducer.

(v) Phased-array ultrasonic techniques may be used to estimate the tissue thickness.

System Description

Reference is initially made to FIG. 1, which is a schematic pictorial illustration of a system 20 for cardiac ablation treatment, in accordance with an embodiment of the present invention. An operator 28 (such as an interventional cardiologist) inserts an intra-body probe, such as a catheter 22, via the vascular system of a patient 26, into a chamber of the patient's heart 24. For example, to treat atrial fibrillation, the operator may advance the catheter into the left atrium and bring an ablation electrode 30 at a distal end of the catheter into contact with myocardial tissue that is to be monitored and/or ablated.

Catheter 22 is connected at its proximal end to a console 32. Console 32 comprises a radiofrequency (RF) energy generator 34, which supplies electrical power via catheter 22 to ablation electrode 30 in order to ablate the target tissue. An irrigation pump 38 supplies an irrigating fluid, such as a saline solution (e.g., a normal saline solution), through catheter 22 to ablation electrode 30. A second radiofrequency generator, RF-US generator 40, supplies electrical power via catheter 22 to an ultrasound transducer disposed within the cavity of the ablation electrode. As further described hereinbelow, the ultrasound transducer is used to estimate the thickness of the myocardial tissue. In response to the estimate, a processor 36 may set a property of the ablating current, such as a magnitude, power, or duration of the current, by controlling RF energy generator 34, either automatically or in response to inputs from operator 28.

Before, during, and/or after the procedure, an electrocardiogram (ECG) recorder 60 may record an ECG of the patient.

Figure 2:
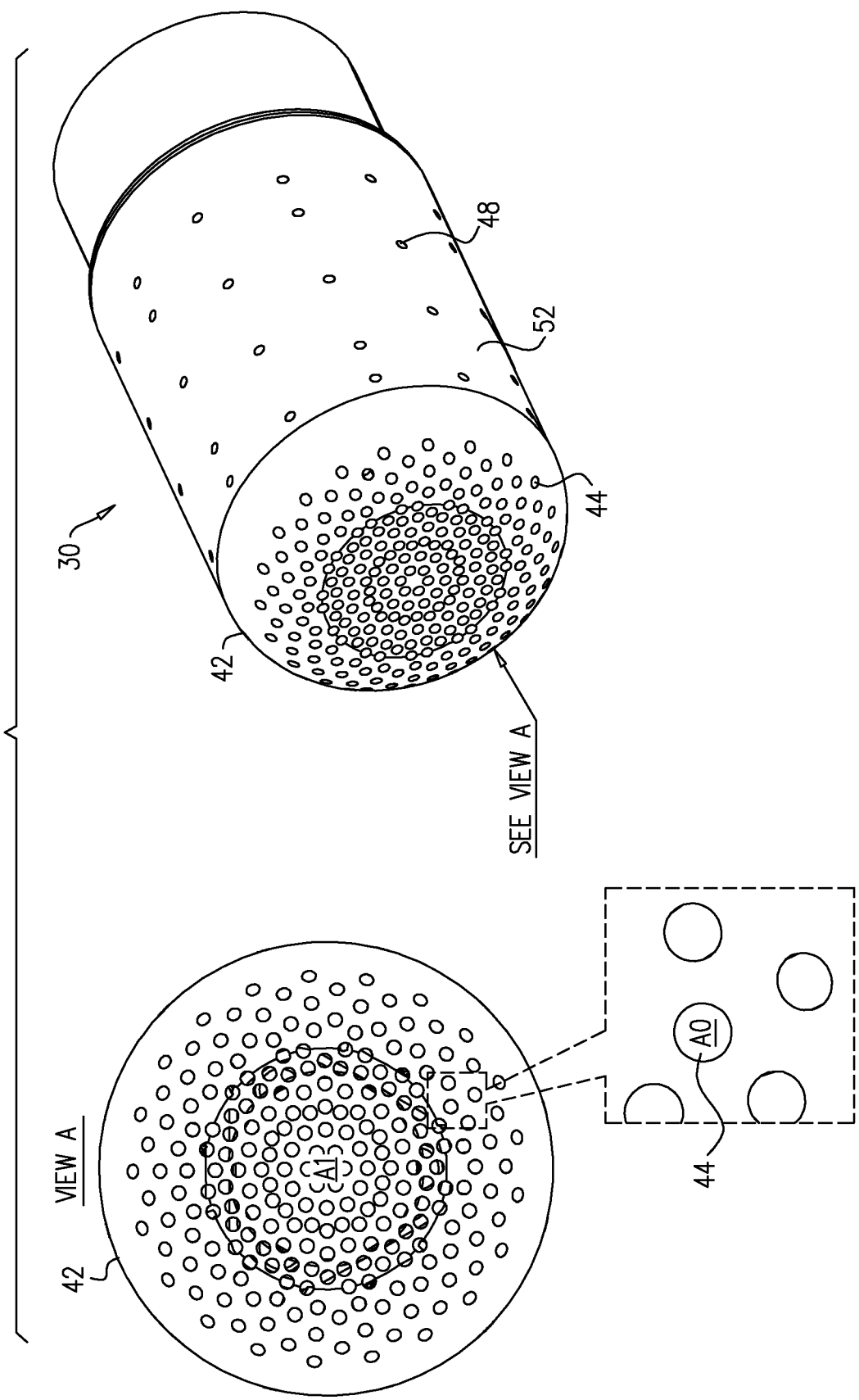
FIGS. 2-5 are schematic illustrations of ablation electrodes, in accordance with some embodiments of the present invention.
Figure 3:
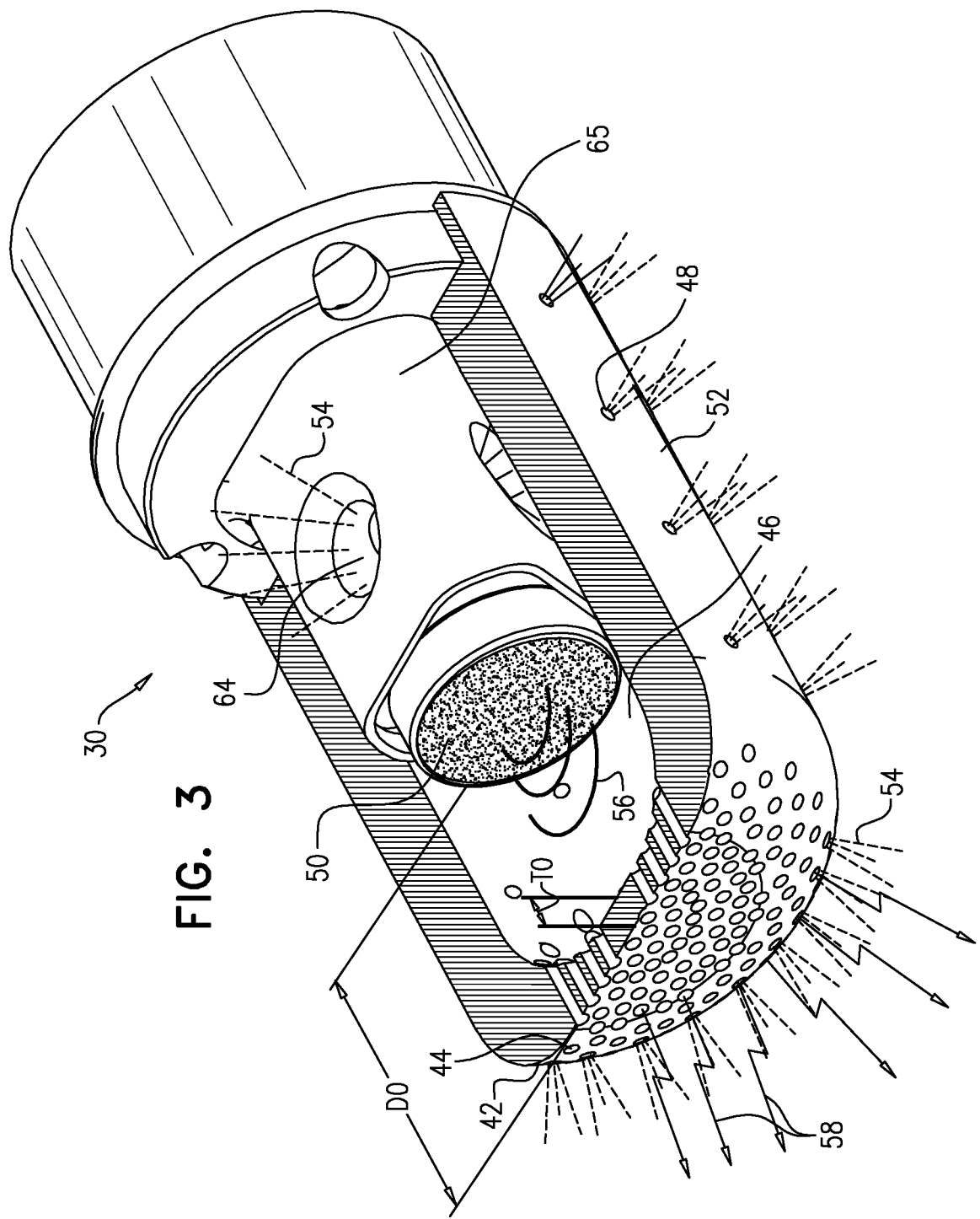

Reference is now made to FIGS. 2 and 3, which are schematic illustrations of ablation electrode 30 (FIG. 1), in accordance with some embodiments of the present invention.

As shown in FIG. 2, ablation electrode 30 comprises a distal face 42, shaped to define a plurality (and in particular, a relatively large number) of apertures 44. For example, distal face 42 may be hyper-apertured in that the distal face is shaped to define at least 100 (e.g., at least 200) apertures. Distal face 42 is typically metallic, such that the distal face may be used to pass an ablating current into the tissue. In particular, the ablating current may be passed from between the apertures.

Typically, the total surface area of apertures 44 is at least 20% (e.g., at least 30% or 40%), but typically less than 50%, of the total surface area A1 of distal face 42. (In other words, distal face 42 is typically at least 20% "open.") For example, if there are N apertures, each having surface area A0, N*A0 may be between 20% and 50% of A1. The total surface area of the apertures is (i) large enough such that ultrasound waves may pass through the distal face without being overly attenuated, but (ii) small enough such that the distal face is mechanically robust, and is further able to pass an ablating current into tissue and/or sense electrical activity of the tissue. Typically, for each of apertures 44, A0 is less than 0.2% (e.g., less than 0.15% or 0.1%) of A1.

In one particular example embodiment, A0 may be approximately 0.0044 mm2, A1 may be approximately 4.9 mm2, and N may be approximately 230. For such an example embodiment, the total surface area of the apertures is slightly greater than 20% of the total surface area of the distal face.

Typically, the distal face is relatively thin, in order to reduce attenuation of the ultrasound waves as the waves pass through the apertures. For example, the thickness T0 of the distal face may be at least 0.015 mm and/or less than 0.5 mm, e.g., between 0.075 and 0.5 mm, such as approximately 0.2 mm. The provision of a relatively thin distal face may also reduce the time required to form the large number of apertures in the distal face.

As shown in FIG. 3, in which part of ablation electrode 30 is "cut away," ablation electrode 30 is shaped to define a cavity 46. Apertures 44, along with, optionally, other apertures 48 along a side wall 52 of ablation electrode 30, provide for fluid communication between cavity 46 and the area that surrounds the ablation electrode. In some embodiments (unlike the embodiment shown in FIGS. 2-3), side wall 52 is hyper-apertured, i.e., side wall 52 is shaped to define a relatively large number of apertures 48.

As further shown in FIG. 3, at least one ultrasound transducer 50 is disposed within cavity 46. In some embodiments, a plurality of ultrasound transducers, such as a one-dimensional or two-dimensional array of ultrasound transducers, are disposed within cavity 46; in other embodiments, as shown in FIG. 3, a single ultrasound transducer is disposed within the cavity. Typically, transducer 50 is disposed a distance D0 of at least 0.5 mm (e.g., at least 1 mm, and/or less than 1.5 mm, such as between 1 and 1.5 mm) from distal face 42. (D0 is typically at least as large as the "dead zone" of the ultrasound transducer.)

Transducer 50 is used to estimate the thickness of the tissue of the patient, by transmitting an ultrasound wave 56 through the apertures and toward the tissue, and detecting reflections from the tissue and tissue boundaries. In response to the reflections, the tissue thickness is estimated. The estimation may be performed, for example, by processor 36 (FIG. 1). Moreover, in response to the estimate, processor 36 may set a property of the ablating current, such as a magnitude, power, or duration of the current, by controlling RF energy generator 34, either automatically or in response to inputs from operator 28.

In some embodiments, ultrasound wave 56 is transmitted prior to the passing of the ablating current. In such embodiments, subsequently to estimating the thickness of the tissue, ablating current 58 is passed from the ablation electrode (e.g., at least from distal face 42 of the electrode, such as from the entire surface of the electrode), into the tissue. Alternatively or additionally, at least one ultrasound wave may be transmitted while passing the ablating current into the tissue, thus allowing the property of the ablating current to be appropriately adjusted in response to any changes in tissue thickness. (Such changes may be caused, for example, by edema, which may cause the wall thickness to increase during the ablation procedure.) For example, an ultrasound wave may be transmitted, and the tissue thickness may be estimated, continually throughout the procedure.

While passing the ablating current into the tissue, irrigating fluid 54 (e.g., a saline fluid, such as a normal saline fluid) may be passed out of the ablation electrode, through apertures 44 and/or apertures 48. In the embodiment shown in FIG. 3, ablation electrode 30 is coupled to fluid-delivery channels 64 having openings in the transducer support 65, channels 64 delivering fluid 54 from pump 38 (FIG. 1) to cavity 46 (and hence, to the apertures). In other embodiments, the openings in transducer support 65 are used to hold additional, "side-facing" ultrasound transducers, and the irrigating fluid flows into cavity 46 via other fluid-delivery channels.

In some embodiments, before, during, and/or after the passing of the ablating current into the tissue, distal face 42 is used to sense electrical activity of the tissue. In such embodiments, distal face 42 may be connected, via catheter 22, to ECG recorder 60 (shown in FIG. 1), which detects the small voltage that is generated by the tissue.

To manufacture ablation electrode 30, distal face 42 is formed at the distal end of a hollow element. For example, distal face 42 may be formed by making a relatively large number (e.g., at least 100 or 200) perforations in the distal end of the element. The scope of the present invention includes any suitable technique for making the perforations, including, for example, electrical discharge machining and/or laser drilling. To complete the formation of the ablation electrode, transducer 50 is coupled to transducer support 65, transducer support 65 is placed inside the cavity of the hollow element, and a fluid-delivery channel is coupled to the element. (The above three steps may be performed in any suitable order. Moreover, each of the above steps may be performed before the formation of the distal face, or after the formation of the distal face.)

Figure 4:
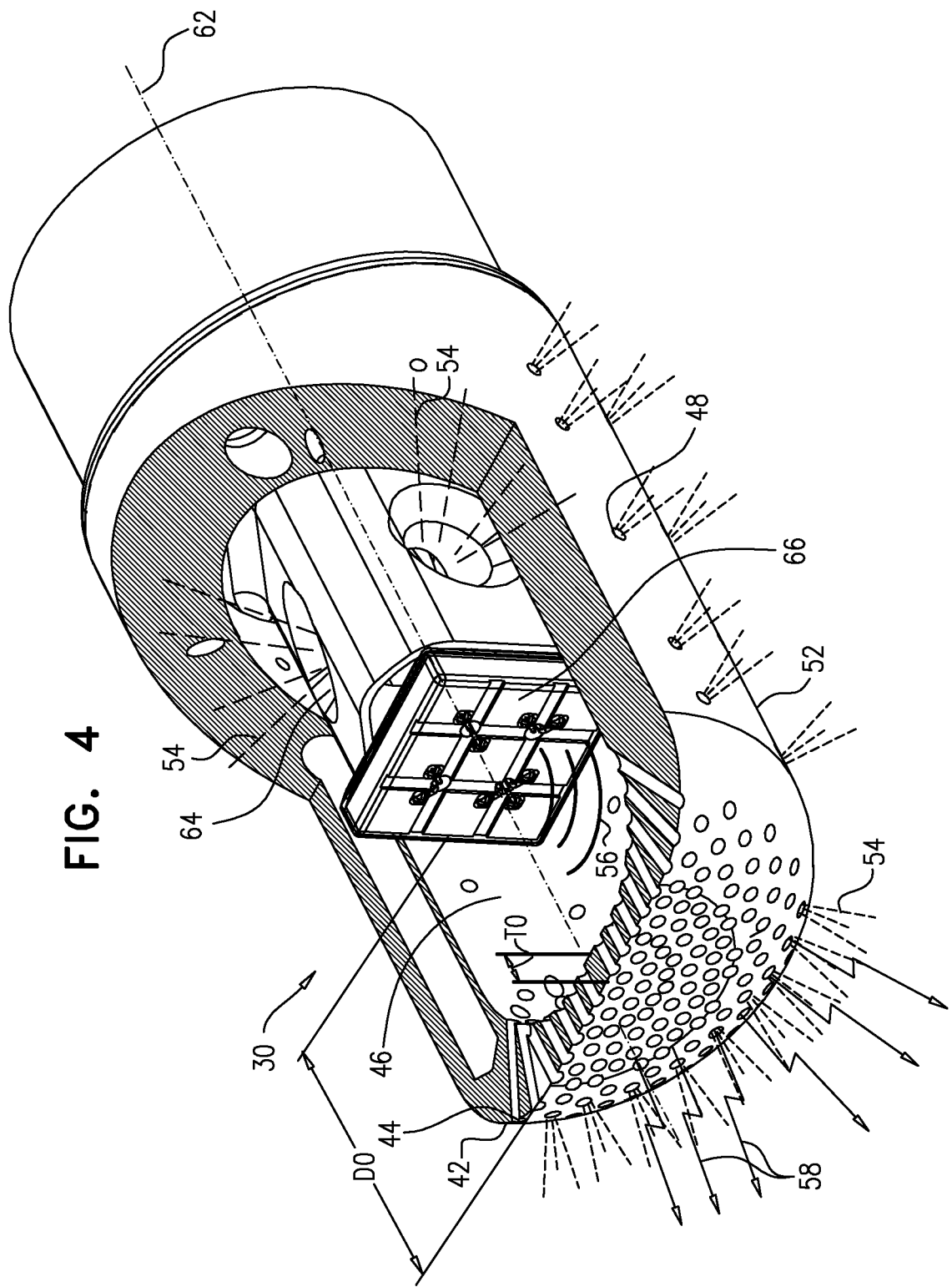

Reference is now made to FIG. 4, which is a schematic illustration of an ablation electrode, in accordance with some embodiments of the present invention. As noted above, in some embodiments, a plurality of ultrasound transducers, such an array of ultrasound transducers, are disposed within cavity 46. For example, FIG. 4 shows a two-dimensional rectilinear array 66 of ultrasound transducers. In such embodiments, beam steering techniques, e.g., phased-array ultrasonic techniques, may be used to estimate the tissue thickness. For example, the transducers may be used to transmit an ultrasonic beam at a non-zero angle with respect to the central longitudinal axis 62 of ablation electrode 30, as shown in FIG. 4. (In other words, the beam may be directed at least partly off to the side, instead of straight ahead.) The thickness of the tissue may then be estimated, in response to reflections of the ultrasonic beam.

Figure 5:
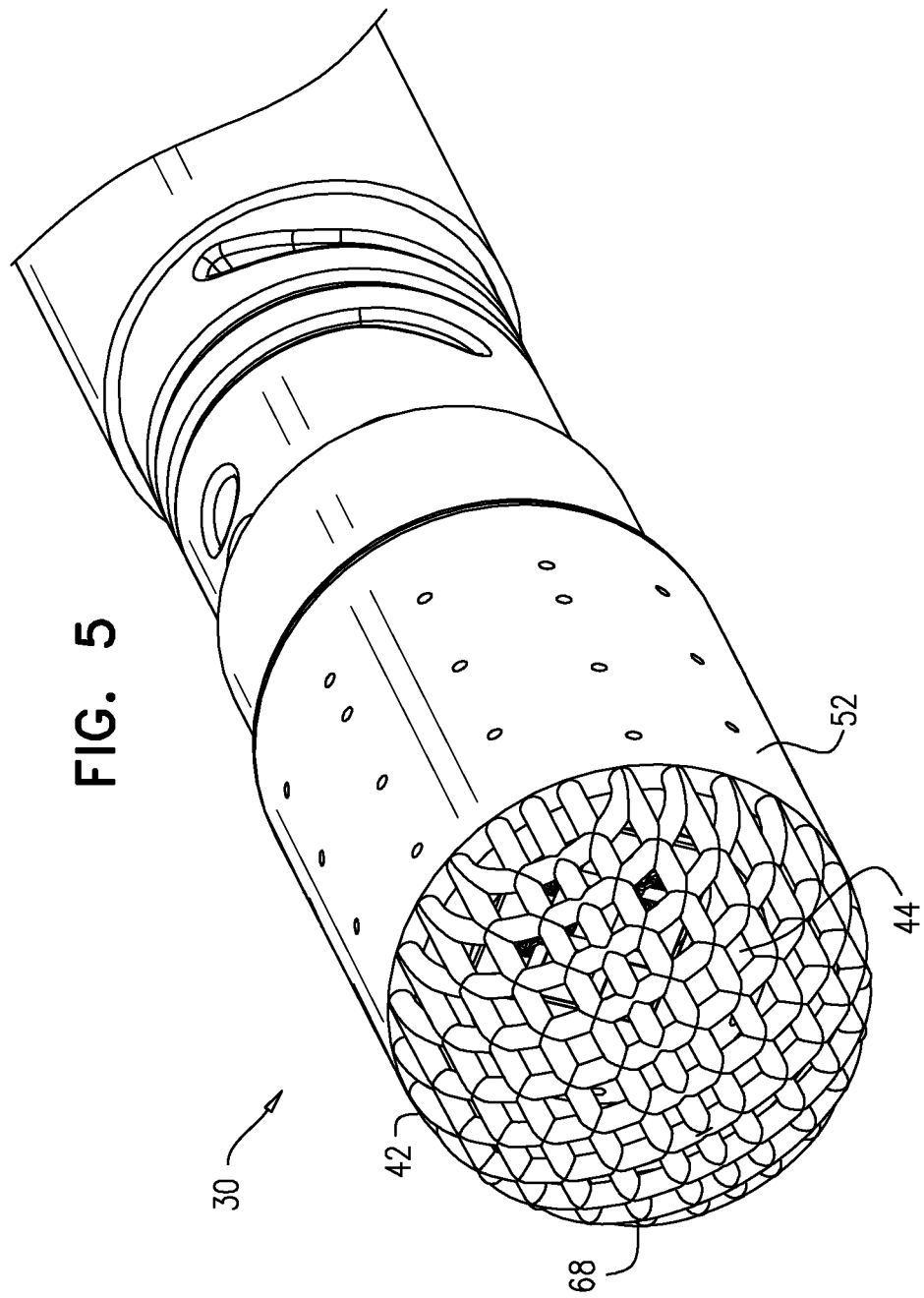

Reference is now made to FIG. 5, which is a schematic illustration of an ablation electrode 30, in accordance with some embodiments of the present invention. In some embodiments, to form distal face 42, a mesh 68, which defines apertures 44, is attached at the distal end of a hollow element, such as by being laser-welded to the distal end of side wall 52 (somewhat analogously to the placement of a membrane over a drum). In some embodiments (not shown), mesh 68 is also attached to scaffolding along the side of the element, such that part of the mesh defines side wall 52.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus comprising:
   an ablation electrode shaped to define a cavity thereof, and comprising a side wall and a metallic distal face;
   a fluid-delivery channel, configured to deliver fluid to the plurality of apertures; and
   at least one ultrasound transducer disposed within the cavity of the ablation electrode, the at least one ultrasound transducer being configured to transmit an ultrasound wave through the plurality of apertures to estimate a thickness of the tissue of a patient by transmitting the ultrasound wave through the plurality of apertures and toward the tissue and detecting reflections from the tissue,
   wherein the metallic distal face comprises a distal-most flat surface, wherein the distal-most flat surface comprises a plurality of apertures,
   wherein the plurality of apertures comprises at least 200 apertures.

2. The apparatus according to claim 1, wherein a surface area of each of the plurality of apertures is less than 0.2% of a total surface area of the metallic distal face.

3. The apparatus according to claim 1, wherein a thickness of the metallic distal face is between 0.075 and 0.5 mm.

4. The apparatus according to claim 1, wherein the at least one ultrasound transducer comprises a plurality of ultrasound transducers.

5. The apparatus according to claim 4, wherein the plurality of ultrasound transducers comprises an array of ultrasound transducers.

6. The apparatus according to claim 1, wherein a total surface area of the plurality of apertures in the metallic distal face is at least 20% of a total surface area of the distal face.

7. The apparatus of claim 1, wherein the plurality of apertures in the metallic distal face allow the ultrasound wave from the at least one ultrasound transducer, and allow the reflections from the tissue, to pass through the metallic distal face without being overly attenuated.

8. The apparatus of claim 1 wherein the plurality of apertures in the metallic distal face have a first density, the side wall comprises a second plurality of apertures having a second density, and the first density is greater than the second density.

* * * * *